US007425171B2

(12) United States Patent
Maupin

(10) Patent No.: US 7,425,171 B2
(45) Date of Patent: Sep. 16, 2008

(54) POST SURGICAL BINDER

(76) Inventor: Kathy Maupin, 567 N. Spoede Rd., St. Louis, MO (US) 63141

( * ) Notice: Subject to any disclaimer, the term of this patent is extended or adjusted under 35 U.S.C. 154(b) by 442 days.

(21) Appl. No.: 10/778,299

(22) Filed: Feb. 13, 2004

(65) Prior Publication Data
US 2005/0181705 A1 Aug. 18, 2005

(51) Int. Cl.
*A41C 1/08* (2006.01)
(52) U.S. Cl. .................... 450/155; 450/96
(58) Field of Classification Search ................ 450/155, 450/96–112; 2/400–403, 228, 238, 455; 602/19, 67–72; 128/98.1–101.1
See application file for complete search history.

(56) References Cited

U.S. PATENT DOCUMENTS

| | | | |
|---|---|---|---|
| 1,477,918 A | 12/1923 | Spilman | |
| 2,310,864 A | 2/1943 | Pegg | |
| 3,298,366 A | 1/1967 | Moore et al. | |
| 3,307,535 A * | 3/1967 | Locke | 602/19 |
| 3,603,316 A * | 9/1971 | Lehman | 450/122 |
| 3,783,879 A | 1/1974 | Stalder | |
| 3,920,008 A | 11/1975 | Lehman | |
| 3,931,816 A * | 1/1976 | Waldmann | 602/19 |
| 4,022,197 A | 5/1977 | Castiglia | |
| 4,697,592 A * | 10/1987 | Maddux et al. | 450/155 |
| 4,787,381 A | 11/1988 | Hubbard et al. | |
| 5,060,639 A | 10/1991 | Marcus | |
| 5,425,702 A | 6/1995 | Carn et al. | |
| 5,533,963 A | 7/1996 | Hall | |
| 5,571,039 A | 11/1996 | Ford | |
| 5,599,290 A | 2/1997 | Hayes et al. | |
| 5,928,175 A | 7/1999 | Tanaka | |
| 6,080,038 A * | 6/2000 | Sano | 450/155 |
| 6,080,125 A | 6/2000 | Mott | |
| 6,270,469 B1 | 8/2001 | Mott | |
| 6,309,369 B1 | 10/2001 | Lebovic | |
| 6,342,044 B1 | 1/2002 | Frangi et al. | |
| 6,454,628 B1 | 9/2002 | Shunichirou | |
| 6,622,719 B1 * | 9/2003 | Slautterback et al. | 128/98.1 |
| 6,629,038 B1 * | 9/2003 | Gressel | 702/19 |

* cited by examiner

*Primary Examiner*—Gloria Hale
(74) *Attorney, Agent, or Firm*—Dennis J. M. Donahue, III; Husch Blackwell Sanders LLP

(57) ABSTRACT

The invention is a post-operative binder designed primarily for female patients made of relatively elastic and padded material. The present invention is designed to put pressure on the Pfannenstiel incisional area to prevent swelling through the use of a primary fastener and cross straps. Cross straps are fixedly attached to the midline section of the binder and removably attach to the sides of the binder at an angle to apply the appropriate pressure to the incisional area. The invention is designed with pockets to accommodate hold hot or cold packs in the incisional area, pain relief devices, sandbags or other hard or soft support structures to apply additional pressure, or drainage receptacles.

51 Claims, 8 Drawing Sheets

POST SURGICAL BINDER

CROSS-REFERENCE TO RELATED APPLICATIONS

None.

STATEMENT REGARDING FEDERALLY SPONSORED RESEARCH OR DEVELOPMENT

Not Applicable

APPENDIX

Not Applicable

BACKGROUND OF THE INVENTION

1. Field of the Invention

The present invention relates generally to medical binders. More specifically the present invention is a post-operative support binder for female patients after vaginal or caesarian deliveries, abdominoplasty, or laparoscopic procedures. The present invention is designed to put pressure on the Pfannenstiel incisional area to prevent swelling. The invention is further designed to hold hot or cold packs, pain relief devices, sandbags to apply additional pressure, or drainage receptacles.

2. Background of the Prior Art

Patients who have undergone abdominoplasty, caesarian sections, or laparoscopic procedures have difficulty with swelling and pain post-operatively. Post operative binders are used to help alleviate this swelling and pain. However, none of the post operative binders revealed in the prior art provides pressure in the Pfannenstiel incisional area to reduce the swelling. Moreover, none of these binders provide pain relief mechanisms such as the incorporation of hot or cold packs or portable medicinal pumps into the binder.

Many of the medical binders revealed in the prior art do not relate to post operative procedures. These binders merely provide back support, abdominal support for pregnant or obese people, hip support, or rib cage protection. For instance, U.S. Pat. No. 5,060,639 issued to Marcus in 1991 teaches a back support adapted to be worn about a person's waist to provide both sacrolumbar support and comfortability to pregnant women or obese people. U.S. Pat. No. 6,454,628 issued to Shunichirou in 2002 discloses a girdle for relieving lumbago (the deterioration and damage of the gluteus maximus muscle) and easing one's lumbar. U.S. Pat. No. 5,571,039 issued to Ford in 1996 teaches an abdominal support which transfers abdominal weight to the shoulders of a pregnant or obese person. U.S. Pat. No. 5,928,175 issued to Tanaka in 1999 discloses a medical corset for compression and protection of the sacroiliac and hip joint regions of a patient. U.S. Pat. No. 4,022,197 issued to Castiglia in 1997 teaches a body support or protection appliance for protection and support of the rib cage area. U.S. Pat. No. 6,342,044 issued to Frangi et al. in 2000 teaches an elastic waistband provided with stiffeners to provide protection in sporting events or protection after an injury. While all of the aforementioned references provide some type of support or protection binder, none of these references provide support in the lower abdominal or pelvic region nor do they address the problem of pain and swelling that occurs post-operatively.

Other references revealed in the prior art do address post operative procedures. However, none of these references apply pressure in the Pfannenstiel region nor do they provide pain relief mechanisms. For instance, U.S. Pat. No. 5,533,963 issued to Hall in 1996 teaches a dressing holder providing non-constrictive dressing for the abdomen and accommodates bags, drains, and other devices exiting the abdominal wall. Because the '963 patent teaches a non-constrictive dressing, it does not teach the application of any pressure to the wound area. U.S. Pat. No. 5,425,702 issued to Carn et al. in 1995 teaches a soft tissue support garment for hip and shoulder wounds, and therefore, does not teach the application of pressure to the Pfannenstiel region. U.S. Pat. No. 2,310,864 issued to Pegg in 1941 teaches an abdominal bandage with a plurality of strips extending outwardly from the back section which are overlapped at a slight angle to increase the adherence to one another. The strips are angled away from the pelvic region and are overlapped to increase adherence not to increase pressure to the abdominal or pelvic region. Accordingly, the '864 patent does not teach the application of pressure to the Pfannenstiel region but actually teaches away from such pressure. U.S. Pat. No. 6,309,369 issued to Lebovic in 2001 teaches a binder to apply pressure to the wound area of a patient who has undergone a mastectomy or other type of chest surgery. However, the '369 patent does not teach any application in the pelvic region. U.S. Pat. No. 3,783,879 issued to Stalder in 1974 teaches a waist support and hip girdle to aid in relieving pain in patients with kidney or spinal injuries. Additionally, the '879 patent teaches the support of the bellies of obese or pregnant people. However, the '879 patent also fails teach the application of pressure in the Pfannenstiel region nor does it disclose a means for pain relief to this region.

Some recent inventions on postoperative binders are teaching the use of inelastic materials instead of elastic materials, such as in U.S. Pat. Nos. 5,599,290 and 6,270,469. Although the '469 patent teaches the reduction of pain by applying support to the incisional area post-operatively, the '469 patent explicitly teaches that mechanical compression should use an inelastic material instead of elastic materials. Additionally, the '469 patent fails to teach the application of pressure to the Pfannenstiel region, and due to the inelastic nature of the binder, the '469 patent does not allow for flexible pockets that can accommodate hot or cold pads or other pain relief devices.

BRIEF DESCRIPTION OF THE INVENTION

It is the main object of the present invention to provide a post-surgical binder that fits the female body and is designed to put pressure on the low transverse incision, i.e. Pfannenstiel incisional area, to prevent swelling. The binder is comprised of a fabric which may be in the form of a wrap or a pair of shorts and comprises a soft material which is preferably elastic and padded material to provide comfort and support.

The binder is designed with a primary fastening means to provide pressure to the incisional area. This fastening means is preferably a cross-over fastener in the midline area of the patient. Additionally, this fastening means is preferably a hook and loop fastener (i.e. Velcro®). The use of the crossover means and a hook and loop fastener allows for a comfortable fit to numerous patients of various sizes and allows for easy adjustment by the patient.

The present invention also may include cross straps fixedly attached to the centerline of the fabric and may removably attach to the side or back of the patient. The cross straps preferably have hook and loop fasteners (i.e. Velcro®). The cross straps attach at various angles and directions to accommodate the curve of the female hip and waist and apply additional pressure to the incisional area.

The binder may also be designed with pockets near the incisional area to hold: 1) cold packs to decrease swelling and increase pain relief, 2) hot packs to increase pain relief, 3) portable medicinal pumps, 4) sandbags to increase pressure to prevent hernias or hematoma, and 5) drainage receptacles to collect drainage from the incisional area. These pockets consist of a swimsuit material which is stretchy in four directions. Moreover, these pockets prevent the on-Q devices and drainage receptacles from getting caught on objects, therefore, preventing injury

DESCRIPTION OF THE PREFERRED EMBODIMENT

Figure 1:
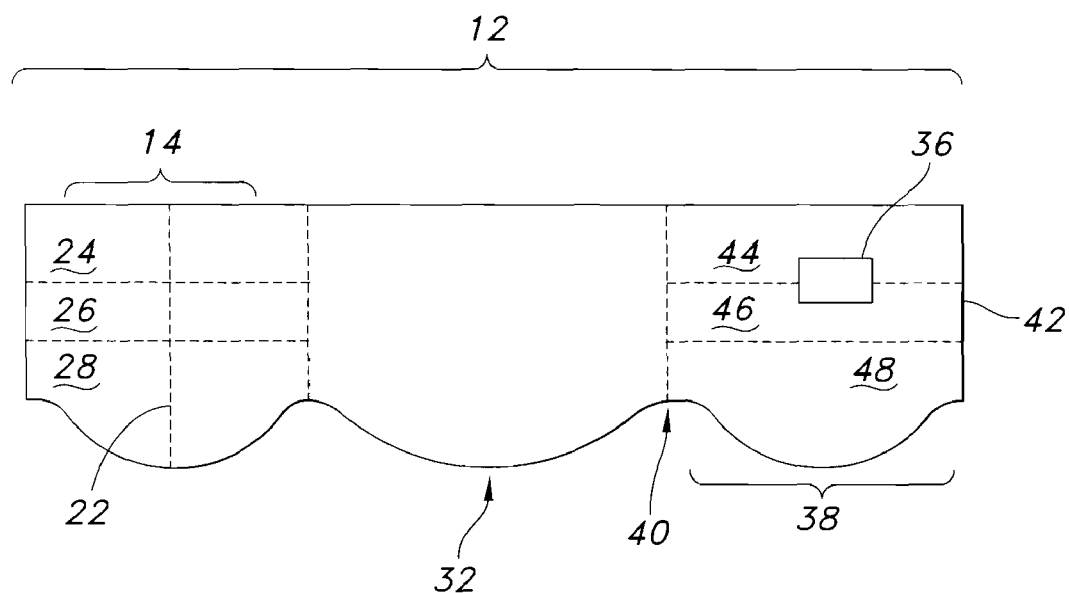
FIG. 1 illustrates a plane view of the exterior of the present invention wherein the abdominal binder is in the shape of a girdle.

As shown in FIGS. 1-11, the preferred embodiment of a personal support device (10) generally includes an abdominal binder (12) having a front section (14), a first side section (16), a second side section (18), and a back section (20). The front section (14) preferably has a center region (22) with an upper portion (24), a middle portion (26) and a lower portion (28). The abdominal binder (12) preferably has an interior side (30) and an exterior side (32). The preferred embodiment also includes an interior pocket (34) and an exterior pocket (36). The interior pocket (34) is preferably attached to the interior side (30) of the abdominal binder (12) while the exterior pocket (36) preferably attached to the exterior side (32) of the abdominal binder (12).

The interior pocket (34) is preferably made of an elastic material and has a liner between the elastic material and the interior side (30) of the abdominal binder (12). Additionally, the interior pocket (34) may be attached in the lower portion (28), middle portion (26), or upper portion (24) of the center region (22) of the front section (14) of the abdominal binder (12) (See FIGS. 3 and 8). The embodiment may also include both lower (34a) and upper interior pockets (34b) (See FIGS. 2 and 11).The interior pocket (34) is preferably closed toward the lower portion (28) of the abdominal binder and open toward the upper portion (24) of the abdominal binder. The interior pocket (34) may be designed to house a comfort device or post-operative device including, but not limited to, the following: a sandbag, a cold pack, a warm pack, a hard support structure, a soft support structure, padding, or an inelastic support structure. Therefore, the pocket, housed with a comfort or a post-operative device, may aid in adding additional pressure to the wound area or provide pain relief to the patient.

The exterior pocket (36) is preferably comprised of an elastic material and closed toward the lower portion (28) of the abdominal binder (12) and open toward the upper portion (24) of the abdominal binder (12). This exterior pocket (36) is preferably comprised of an elastic material. Additionally, the exterior pocket (36) is designed to support a number of post-operative devices including, but not limited to, the following: a pain relief device, such as an On-Q pain relief pump, or a drainage receptacle. The use of the exterior pocket helps prevent such pain relief devices or drainage receptacles from getting caught on objects and pulled out of the patient.

The preferred embodiment also includes a support strap (38) having a proximate end (40), a distal end (42), and an upper section (44), middle section (46) and a lower section (48). The support strap (38) is preferably attached at its proximate end (40) to the abdominal binder (12). Preferably, the support strap's upper section (44), middle section (46) and lower section (48) extend to its distal end (42) and respectively overlaps the abdominal binder's upper portion (24), middle portion (26), and lower portion (28). The support strap's upper section (44), middle section (46) and lower section (48) preferably are of relatively equal width to the abdominal binder's upper portion (24), middle portion (26), and lower portion (28). In the preferred embodiment, a support fastener (50) selectively connects the distal end (42) of the support strap (38) to the abdominal binder (12). This overlap feature and the selective connection allows the binder to conform to the shape of the wearer. Further, the equal width of the support strap and front section of the binder provides allows coverage and support from the pelvic region up to the lower abdomen region.

In the preferred embodiment, a first cross strap (52) is attached to the abdominal binder (12) at the center region (22) of the front section (14). The first cross strap (52) preferably has a first distal end (54) that extends toward the first side section (16) of the abdominal binder (12). The first cross strap's first distal end (54) preferably has a first fastener (56) for selective connection to the exterior side (32) of the abdominal binder (12). The preferred embodiment also has a second cross strap (58) attached to the abdominal binder (12) at the center region (22) of the front section (14). The second cross strap (58) preferably has a second distal end (60) extending toward the second side section (18) of the abdominal binder (12). The second cross strap's second distal end (60) preferably has a second fastener (62) for selective connection to the exterior side (32) of the abdominal binder (12).

These two cross straps provide extra support to the wearer. Additionally, the selective connections allow the wearer to adjust the connection to ensure that pressure is placed in the appropriate places. Additionally, the cross straps may be attached to the upper (24), middle (26), or lower (28) portions of the center region (22) of the front section (14) of the abdominal binder (12).

In the preferred embodiment (see FIG. 6), the first cross strap (52) has a lower cross strap (52a) and a middle cross strap (52b) which attach to the lower portion (28) and middle portion (26) of the center region (22). The second cross strap (58) also has a lower cross strap (58a) and a middle cross strap (58b) which attach to the lower portion (28) and middle portion (26) of the center region (22). The first fastener (56) and second fastener (62) respectively connect at the first distal end and second distal end above the lower portion (28) of the center section (22). The first cross strap (52) and second cross strap (58) may also be attached to the middle portion (26) and upper portion (24) of the center region (22) (See FIG. 10). Further, the embodiment may include both an upper and lower set of cross straps (See FIGS. 7 and 9). The use of both upper and lower cross straps will aid in the support and pressure to the correct regions of the pelvic and lower abdominal regions.

In the preferred embodiment, the abdominal binder (12), first cross strap (52), second cross strap (58), support strap (38), interior pocket (34), or exterior pocket (36) are made of an elastic material. However, an embodiment may also exist in which only one or more of these elements are made of an elastic material. Additionally, the personal support device (10) preferably has an inelastic padding material that is attached to the center region (22) of the abdominal binder (12). This inelastic padding adds comfort for the wearer. Preferably, the support strap's distal end (54) overlaps at least a portion of the inelastic padding material. This overlapping feature ensures adequate support, comfort to the wearer, and adequate pressure to the Pfannenstiel region.

Figure 9:
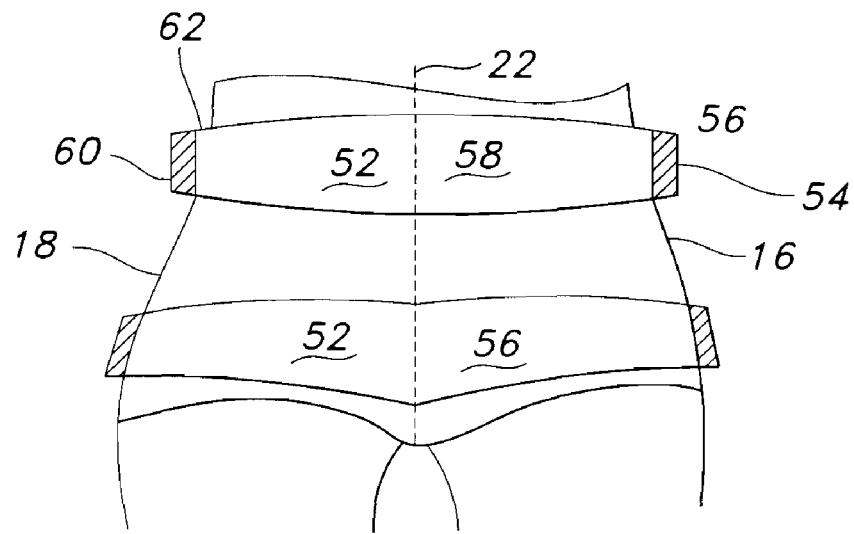
FIG. 9 illustrates an isometric view of the present invention as it is used on a patient wherein the fabric is in the shape of a girdle and the first and second cross straps are located in the middle and upper portions of the binder.
Figure 10:
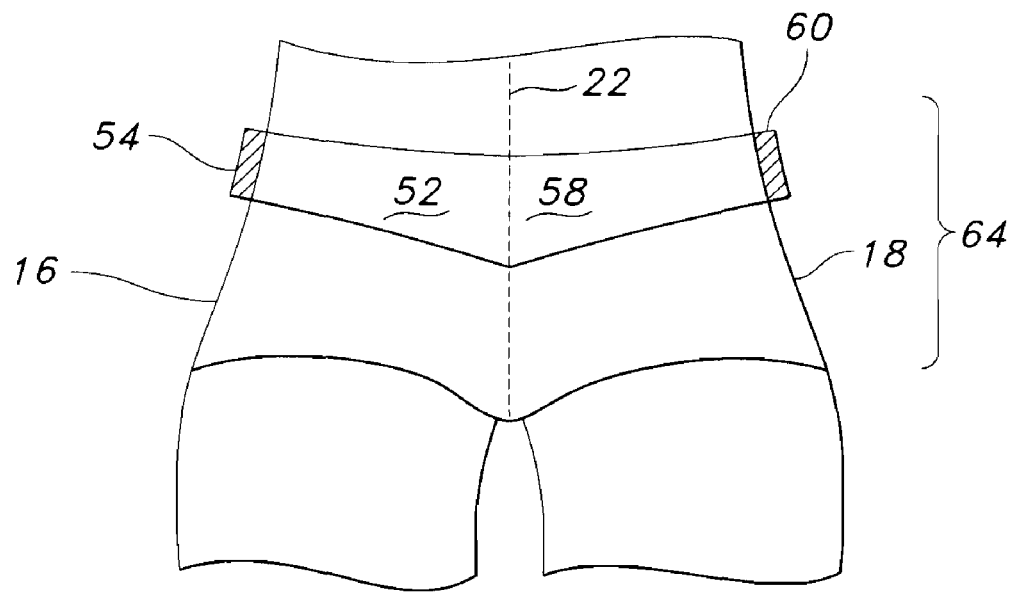
FIG. 10 illustrates an isometric view of the present invention as it is used on a patient wherein the binder is in the shape of a pair of shorts.
Figure 11:
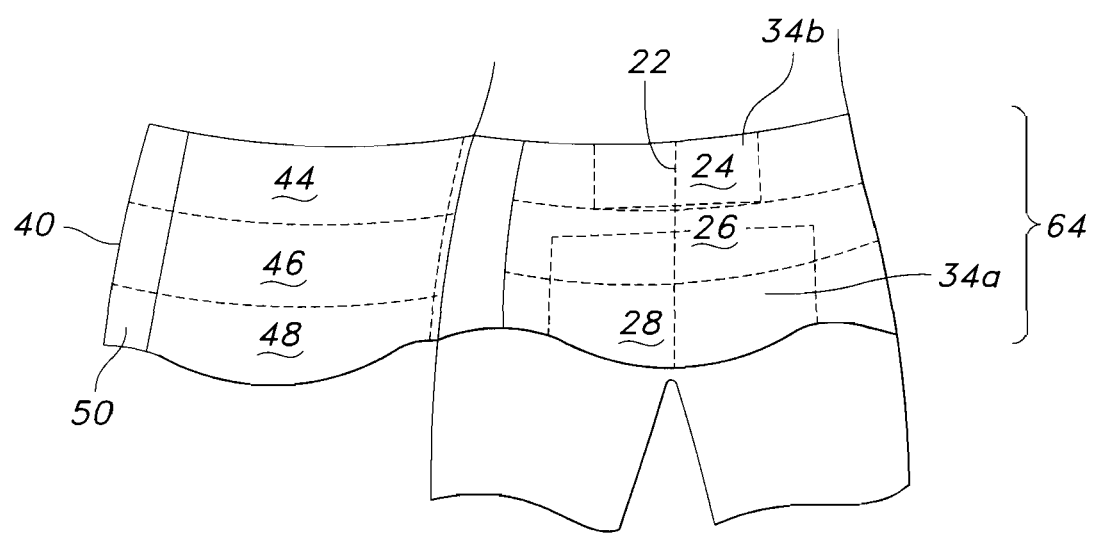
FIG. 11 illustrates an isometric view of the present invention as it is used on a patient wherein the fabric is in the shape of a pair of shorts and the support strap has not been fastened.

As shown in the Figures, the preferred embodiment of the personal support device may be formed in the shape of a girdle (see FIGS. 1-6) or a pair of shorts (64) (see FIGS. 9 & 10).

Figure 4:
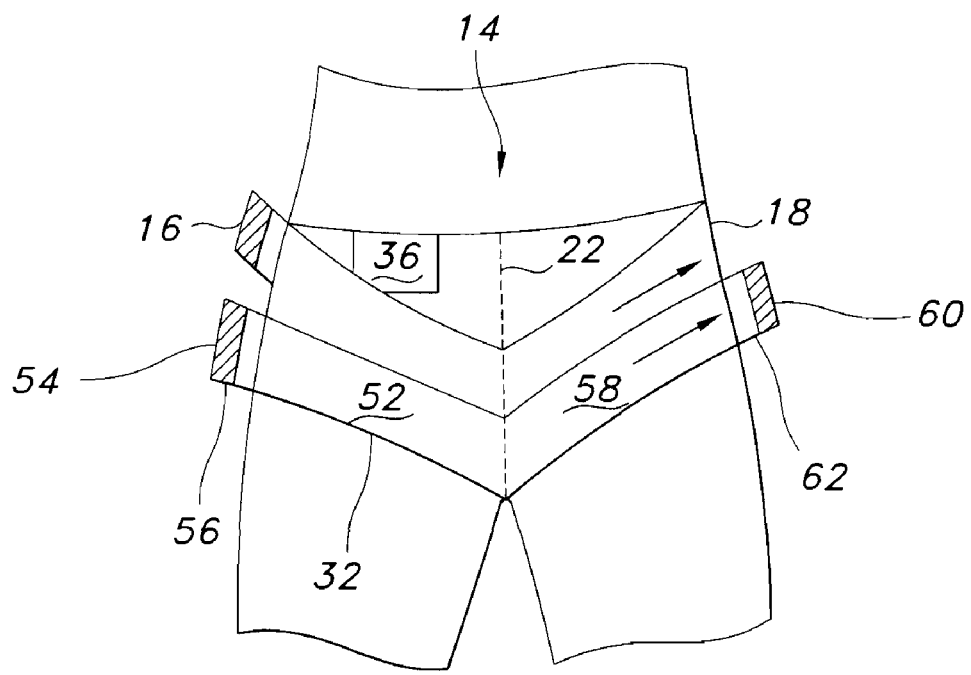
FIG. 4 illustrates an isometric view of the front section, first side section, and second side section of the present invention as it is used on a patient wherein the fabric is in the shape of a girdle and the first and second side straps have not been fastened.
Figure 5:
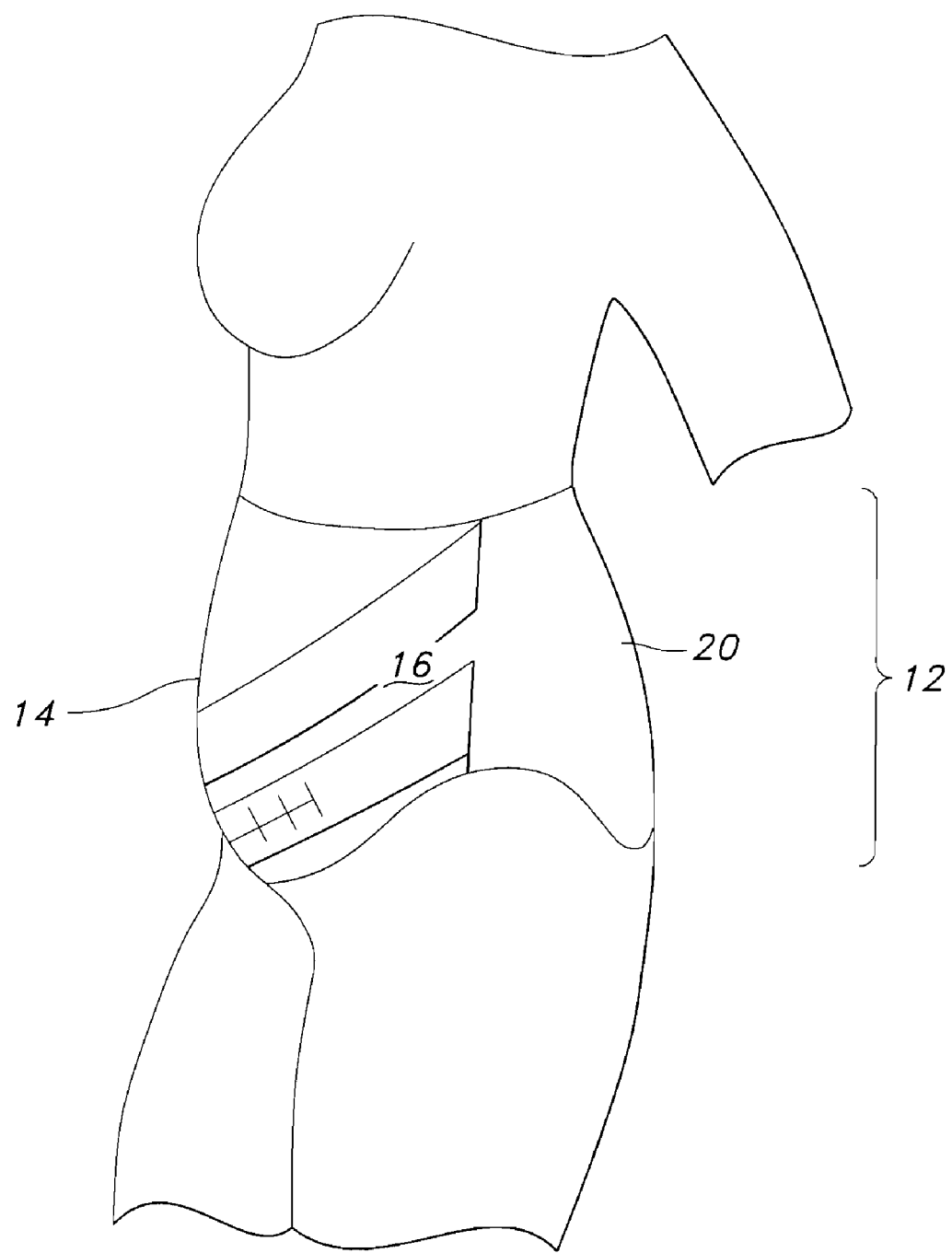
FIG. 5 illustrates a side view of the present invention as it is used on a patient wherein the fabric is in the shape of a girdle
Figure 6:
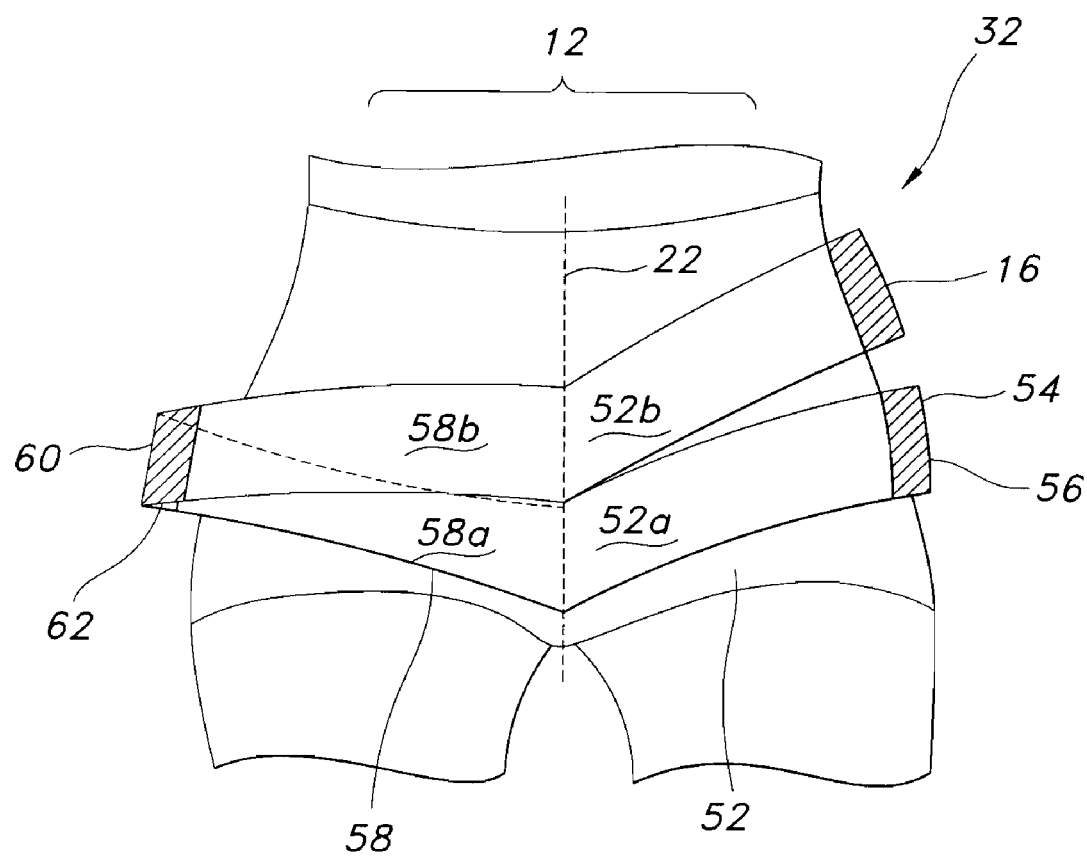
FIG. 6 illustrates an isometric view of the present invention as it is used on a patient wherein the fabric is in the shape of a girdle and the first and second cross straps have not been fastened.

FIG. 4 illustrates another embodiment of a personal support device which includes an abdominal binder having a front section (14), a first side section (16), a second side section (18), and a back section (20). The front section (14) has a center region (22) with an upper portion (24), a middle portion (26), and a lower portion (28). The abdominal binder (12) also has an interior side (30) and an exterior side (32). In this embodiment, a first cross strap (52) is attached to the abdominal binder (12) at the center region (22) of the front section (14) and has a first distal end (54) extending toward the first side section (16). This first distal end (54) further has a first fastener (56) that selectively connects to the exterior side (32) of the abdominal binder (12). In this embodiment, there is also a second cross strap (58) attached to the abdominal binder (12) at the center region (22) of the front section (14). The second cross strap (58) has a second distal end (60) extending toward the second side section (18). This second distal end (60) has a second fastener (62) that selectively connects to the exterior side (32) of the abdominal binder (12). In this embodiment, at least one of the abdominal binder (12), the first cross strap (52) and the second cross strap (58) are comprised of an elastic material.

Figure 2:
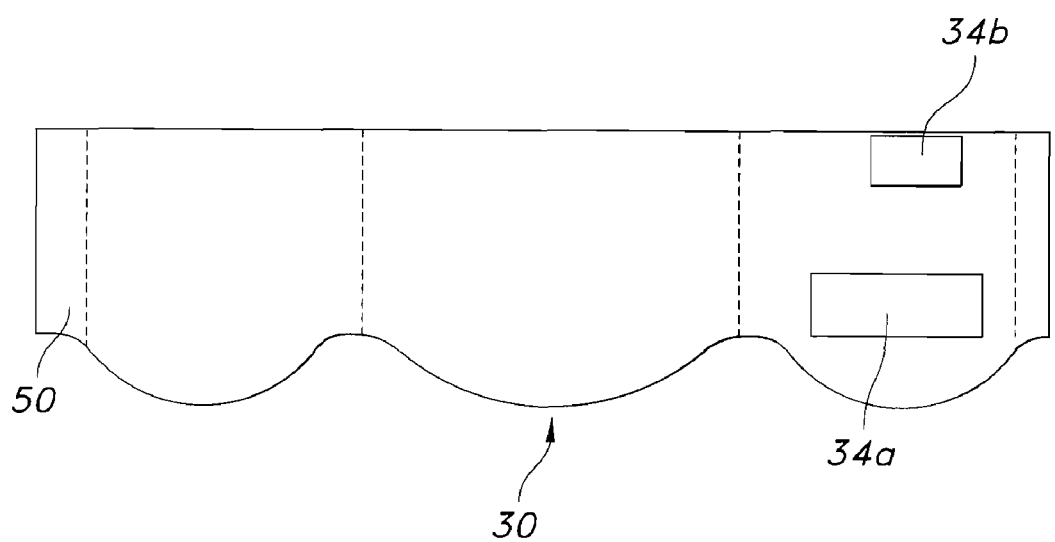
FIG. 2 illustrates a plane view of the interior of the present invention wherein the abdominal binder is in the shape of a girdle.
Figure 3:
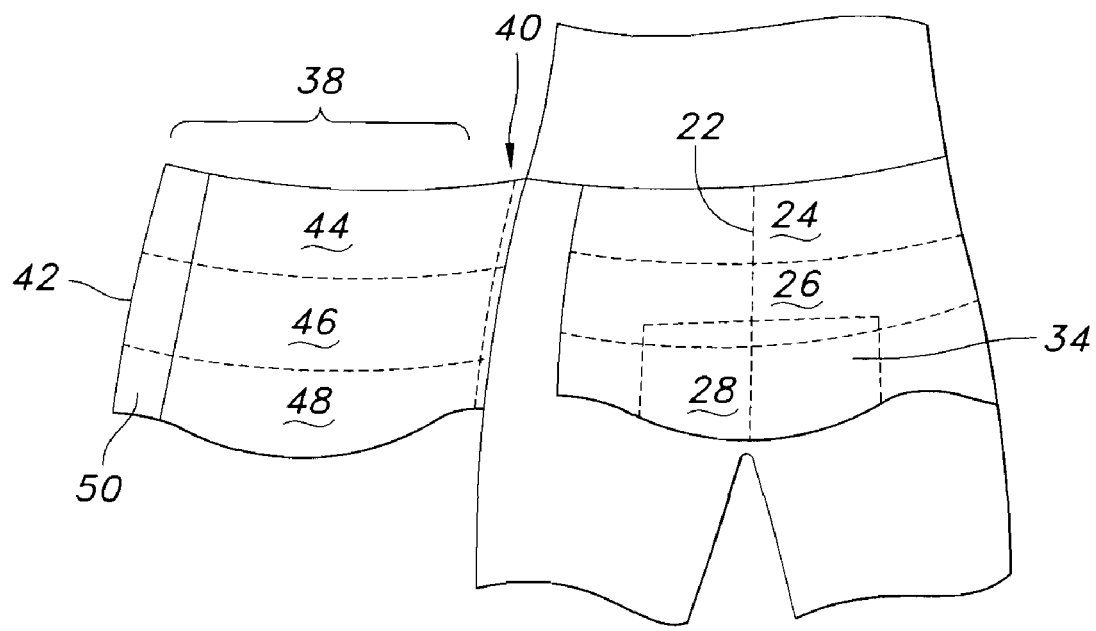
FIG. 3 illustrates an isometric view of the present invention wherein the fabric is in the shape of a girdle and the support strap has not been fastened.

FIGS. 2 and 3 illustrate yet another embodiment of a personal support device which includes an abdominal binder having a front section (14), a first side section (16), a second side section (18), and a back section (20). The front section (14) has a center region (22) with an upper portion (24), a middle portion (26), and a lower portion (28). This embodiment also includes a support strap (38) which has a proximate end (40), a distal end (42), an upper section (44), a middle section (46), and a lower section (48). This support strap (38) is attached at its proximate end (40) to the abdominal binder (12). The upper section (44), middle section (46) and lower section (48) extend to the distal end (42) of the support strap and respectively overlap the upper portion (24), middle portion (26) and lower portion (28) of the abdominal binder. The embodiment also has a support fastener (50) which selectively connects the distal end (42) of the support strap (38) to the abdominal binder (12). The embodiment also includes a first cross strap (52) which is attached to the abdominal binder (12) at the center region (22) of the front section (14) and has a first distal end (54) extending toward the first side section (16) of the abdominal binder (12). The first distal end (54) further has a first fastener (56) for selective connection to the exterior side (32) of the abdominal binder (12). Finally, this embodiment has a second cross strap (58) that is attached to the abdominal binder (12) at the center region (22) of the front section (14) and has a second distal end (60) extending toward the second side section (18). This second distal end (60) has a second fastener (62) for selective connection to the exterior side (32) of the abdominal binder (12).

FIG. 1 illustrates another embodiment of a personal support device (10) which includes an abdominal binder (12) having a front section (14), a first side section (16), a second side section (18), and a back section (20). The front section (14) has a center region (22) with an upper portion (24), a middle portion (26) and a lower portion (28). The embodiment has an exterior pocket (36) attached to the exterior side (32) of the abdominal binder (12). The exterior pocket (36) is closed toward said lower portion (28) of said abdominal binder and open toward said upper portion (24) of said abdominal binder.

Figure 7:
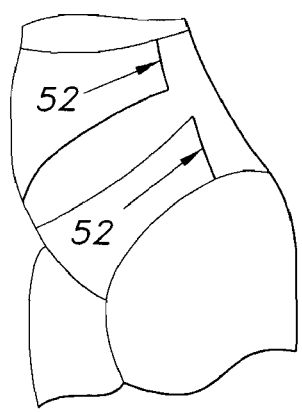
FIG. 7 illustrates an isometric view of the present invention as it is used on a patient wherein the fabric is in the shape of a girdle and the upper and lower cross straps have been fastened.
Figure 8:
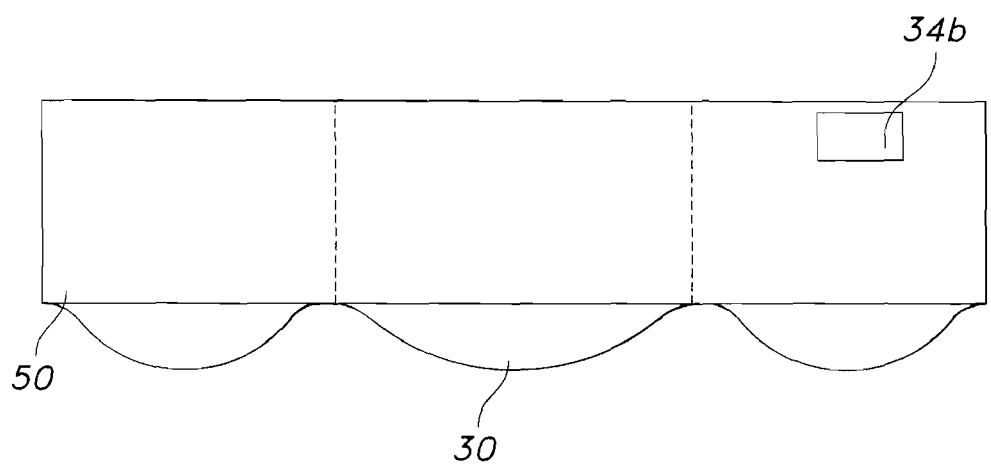
FIG. 8 illustrates a plane view of the interior of the present invention wherein the abdominal binder is in the shape of a girdle.

FIGS. 2 and 7 illustrate another embodiment of a personal support device (10) which includes an abdominal binder (12) with a front section (14), a first side section (16), a second side section (18), and a back section (20). The front section (14) has a center region (22) with an upper portion (24), a middle portion (26) and a lower portion (28). The embodiment also has an interior pocket (34) attached to the interior side (30) of the abdominal binder (12) in the center region (22) of the front section (14). The interior pocket (34) is closed at said lower portion (28) of the abdominal binder (12) and open toward the middle portion (26) of the abdominal binder (12).

According to the preferred embodiment of the girdle-type binder, the support strap (38) is attached at its proximate end (40) to the girdle and is selectively connected at its distal end (42) to the exterior portion (32) of the binder (12). In the preferred embodiment, there is also padding in the front section (14) of the binder which the support strap (38) overlaps. In this case, the padding could also have a fastener at its distal end which selectively connects the girdle ends at the interior portion of the binder, such as in the manner of a double breasted suit (not shown).

One benefit of the invention is that the wearer can adjust the support of the binder using the cross straps and without needing to readjust the support strap. This permits the wearer to optimize the comfort and support of the binder without assistance from other persons.

In view of the foregoing, it will be seen that the several advantages of the invention are achieved and attained. The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, while the present invention is primarily designed to be used as a post-surgical binder, it will be appreciated that embodiments of the present invention may also be used as a girdle or other support device. As yet another example, although the preferred embodiment of the present invention uses hook and loop fasteners for overlapping sections of the binder, it will be appreciated other fasteners may be used in which only the fasteners themselves overlap each other, such as zippers, hooks and eyes, or buttons and holes, as well as any other equivalent type of fastener which may now be known or developed in the future. It will also be appreciated that the fasteners can be used on the girdle-type of binder as well as the shorts-type of binder. Thus, the breadth and scope of the present invention should not be limited by any of the above-described exemplary embodiments, but should be defined only in accordance with the following claims appended hereto and their equivalents.

What is claimed is:

1. A binder for a human body comprising:
an abdominal binder selected from a group of apparel consisting of a girdle and a pair of shorts, said abdominal binder comprising a front section located between a pair of side sections and opposite a back section, said front section comprising a center region with an upper portion, a middle portion and a lower portion, wherein said upper portion, said middle portion and lower portion are relatively equal in width;
a first cross strap attached to said abdominal binder at said center region of said front section and comprising a first distal end extending towards and selectively fastened to one of said side sections at a first location above said lower portion, said first cross strap being attached to said center region below said upper portion and being approximately as wide as at least one of said lower portion and said middle portion; and
a second cross strap attached to said abdominal binder at said center region of said front section and comprising a second distal end extending towards and selectively fastened to another of said side sections at a second location above said lower portion, said second cross strap being attached to said center region below said upper portion and being approximately as wide as at least one of said lower portion and said middle portion.

2. The binder for a human body as in claim 1 further comprising a support strap attached to said abdominal binder, extending between said pair of side sections across said front section and selectively fastened at one of said side sections, wherein said support strap overlaps said upper portion, said middle portion and said lower portion of said abdominal binder and said first cross strap and said second cross strap are connected to said support strap.

3. The binder for a human body as in claim 1 wherein said abdominal binder further comprises an interior side and an exterior side and said front section further comprises a pocket attached to said interior side of said abdominal binder.

4. A binder for a human body comprising:
an abdominal binder having a front section, a first side section, a second side section, and a back section, said front section further comprising a center region with an upper portion, a middle portion and a lower portion, said abdominal binder having an interior side and an exterior side;
a first cross strap attached to said abdominal binder at said center region of said front section and having a first distal end extending toward said first side section, said first distal end further comprising a first fastener for selective connection to said exterior side of said abdominal binder;
a second cross strap attached to said abdominal binder at said center region of said front section and having a second distal end extending toward said second side section, said second distal end further comprising a second fastener for selective connection to said exterior side of said abdominal binder, and
wherein at least one of said abdominal binder, said first cross strap and said second cross strap are further comprised of an elastic material, wherein said front section further comprises an inelastic padding material in said center region and an elastic material overlapping at least a portion of said inelastic padding material such that said portion of inelastic padding material is in said interior side of said abdominal binder and said elastic material is on said exterior side of said abdominal binder.

5. A personal support device comprising:
an abdominal binder for a human body having a front section, a first side section, a second side section, and a back section, said front section further comprising a center region with an upper portion, a middle portion and a lower portion, said abdominal binder having an interior side and an exterior side;
a first cross strap attached to said abdominal binder at said center region of said front section and having a first distal end extending toward said first side section, said first distal end further comprising a first fastener for selective connection to said exterior side of said abdominal binder;
a second cross strap attached to said abdominal binder at said center region of said front section and having a second distal end extending toward said second side section, said second distal end further comprising a second fastener for selective connection to said exterior side of said abdominal binder, and
wherein at least one of said abdominal binder, said first cross strap and said second cross strap are further comprised of an elastic material, wherein said first cross strap further comprises a first lower cross strap and a first middle cross strap respectively attached at said lower portion and said middle portion of said center region, wherein said second cross strap further comprises a second lower cross strap and a second middle cross strap respectively attached at said lower portion and said middle portion of said center region, and wherein said first fastener and said second fastener respectively connect said first distal end and said second distal end above said lower portion of said center section.

6. The personal support device as in claim 5, wherein said abdominal binder is selected from a group of apparel consisting of a girdle and a pair of shorts.

7. The personal support device as in claim 5, wherein said upper portion, said middle portion and lower portion are relatively equal in width.

8. The personal support device as in claim 7, wherein said first lower cross strap and said first middle cross strap are attached proximate to said first fastener and wherein said second lower cross strap and said second middle cross strap are attached proximate to said second fastener.

9. The personal support device as in claim 7, wherein said first cross strap and said second cross strap are approximately as wide as said lower portion and said middle portion.

10. The personal support device as in claim 5, wherein said first lower cross strap and said first middle cross strap are attached proximate to said first fastener and wherein said second lower cross strap and said second middle cross strap are attached proximate to said second fastener.

11. The personal support device as in claim 5, further comprising a pocket attached to said interior side of said abdominal binder in said center region of said front section.

12. The personal support device as in claim 4, further comprising a pocket attached to said interior side of said abdominal binder in said center region of said front section.

13. The personal support device as in claim 5, further comprising a pocket attached to said exterior side of said abdominal binder.

14. The personal support device as in claim 5, further comprising:
a support strap having a proximate end, a distal end, an upper section, and middle section and a lower section, wherein said support strap is attached at said proximate end to said abdominal binder and wherein said upper section, said middle section and said lower section extend to said distal end of said support strap and respectively overlap said upper portion, said middle portion and said lower portion of said abdominal binder; and
a support fastener selectively connecting said distal end of said support strap to said abdominal binder.

15. The personal support device as in claim 5, wherein said front section further comprises an inelastic padding material in said center region and an elastic material overlapping at least a portion of said inelastic padding material such that said portion of inelastic padding material is in said interior side of said abdominal binder and said elastic material is on said exterior side of said abdominal binder.

16. A personal support device comprising:
an abdominal binder for a human body having an exterior side, a front section, a first side section, a second side section, and a back section, said front section further comprising a center region with an upper portion, a middle portion and a lower portion;
a support strap having a proximate end, a distal end, an upper section, and middle section and a lower section, wherein said support strap is attached at said proximate end to said abdominal binder and wherein said upper section, said middle section and said lower section extend to said distal end of said support strap and respectively overlap said upper portion, said middle portion and said lower portion of said abdominal binder;
a support fastener selectively connecting said distal end of said support strap to said abdominal binder;
a first cross strap attached to said abdominal binder at said center region of said front section and having a first distal end extending toward said first side section, said first distal end further comprising a first fastener for selective connection to said exterior side of said abdominal binder;
a second cross strap attached to said abdominal binder at said center region of said front section and having a second distal end extending toward said second side section, said second distal end further comprising a second fastener for selective connection to said exterior side of said abdominal binder.

17. The personal support device as in claim 16, wherein said abdominal binder is selected from a group of apparel consisting of a girdle and a pair of shorts.

18. The personal support device as in claim 16, wherein at least one of said abdominal binder, said first cross strap, said second cross strap and said support strap are further comprised of an elastic material.

19. The personal support device as in claim 16, wherein said abdominal binder, said first cross strap, said second cross strap and said support strap are each comprised of an elastic material.

20. The personal support device as in claim 16, further comprising a pocket attached to said interior side of said abdominal binder in said center region of said front section, said pocket being closed at said lower portion of said abdominal binder and open toward said middle portion of said abdominal binder.

21. The personal support device as in claim 16, further comprising a pocket attached to said interior side of said abdominal binder in said center region of said front section, said pocket being closed at said middle portion of said abdominal binder and open toward said upper portion of said abdominal binder.

22. The personal support device as in claim 16, further comprising a pocket attached to said exterior side of said abdominal binder.

23. The personal support device as in claim 16, wherein said abdominal binder is comprised of a pair of shorts, and wherein said proximate end of said support strap is attached toward said first side of said abdominal binder and said distal end of said support strap overlaps said center region of said front section and extends toward said second side of said abdominal binder for said selective connection to said abdominal binder.

24. A personal support device comprising:
an abdominal binder for a human body having a front section, a first side section, a second side section, and a back section, said front section further comprising a center region with an upper portion, a middle portion and a lower portion, said abdominal binder having an interior side and an exterior side;
a first cross strap attached to said abdominal binder at said center region of said front section and having a first distal end extending toward said first side section, said first distal end further comprising a first fastener for selective connection to said exterior side of said abdominal binder;
a second cross strap attached to said abdominal binder at said center region of said front section and having a second distal end extending toward said second side section, said second distal end further comprising a second fastener for selective connection to said exterior side of said abdominal binder; and
an exterior pocket attached to said exterior side of said abdominal binder, said pocket being closed toward said lower portion of said abdominal binder and open toward said upper portion of said abdominal binder.

25. The personal support device as in claim 24, wherein said exterior pocket is further comprised of an elastic material.

26. The personal support device as in claim 24, wherein said exterior pocket is designed to support a post-operative device.

27. The personal support device as in claim 24, further comprising an interior pocket attached to said interior side of said abdominal binder.

28. The personal support device as in claim 24 wherein said upper portion, said middle portion and lower portion are relatively equal in width and wherein said first cross strap and said second cross strap are approximately as wide as at least one of said lower portion and said middle portion.

29. The personal support device as in claim 24, further comprising:
a support strap having a proximate end, a distal end, an upper section, and middle section and a lower section, wherein said support strap is attached at said proximate end to said abdominal binder and wherein said upper section, said middle section and said lower section extend to said distal end of said support strap and respectively overlap said upper portion, said middle portion and said lower portion of said abdominal binder; and
a support fastener selectively connecting said distal end of said support strap to said abdominal binder.

30. A personal support device comprising:
an abdominal binder for a human body having a front section, a first side section, a second side section, and a back section, said front section further comprising a center region with an upper portion, a middle portion and a lower portion, said abdominal binder having an interior side and an exterior side;
a support strap having a proximate end, a distal end, an upper section, and middle section and a lower section, wherein said support strap is attached at said proximate end to said abdominal binder and wherein said upper section, said middle section and said lower section extend to said distal end of said support strap and respectively overlap said upper portion, said middle portion and said lower portion of said abdominal binder; and
a support fastener selectively connecting said distal end of said support strap to said abdominal binder; and
an exterior pocket attached to said exterior side of said abdominal binder, said pocket being closed toward said lower portion of said abdominal binder and open toward said upper portion of said abdominal binder.

31. The personal support device as in claim 30, further comprising an interior pocket attached to said interior side of said abdominal binder.

32. The personal support device as in claim 31, wherein said interior pocket is attached in said center region of said front section.

33. The personal support device as in claim 31, wherein said interior pocket is further comprised of an elastic material and a liner between said elastic material and said interior side of said abdominal binder.

34. The personal support device as in claim 31, wherein said interior pocket is designed to house a comfort device.

35. The personal support device as in claim 31, wherein said interior pocket further comprises a post-operative device selected from the group of devices consisting of a sandbag, a cold pack, a warm pack, a hard support structure, a soft support structure, padding, and an inelastic support structure.

36. The personal support device as in claim 30, further comprising an exterior pocket attached to said exterior side of said abdominal binder.

37. The personal support device as in claim 30, further comprising:
a first cross strap attached to said abdominal binder at said center region of said front section and having a first distal end extending toward said first side section, said first distal end further comprising a first fastener for selective connection to said exterior side of said abdominal binder; and
a second cross strap attached to said abdominal binder at said center region of said front section and having a second distal end extending toward said second side section, said second distal end further comprising a second fastener for selective connection to said exterior side of said abdominal binder.

38. The personal support device as in claim 37 wherein said upper portion, said middle portion and lower portion are relatively equal in width and wherein said first cross strap and said second cross strap are approximately as wide as at least one of said lower portion and said middle portion 39. A personal support device comprising:
an abdominal binder for a human body having a front section, a first side section, a second side section, and a back section, said front section further comprising a center region with an upper portion, a middle portion and a lower portion, said abdominal binder having an interior side and an exterior side;
an interior pocket attached to said interior side of said abdominal binder;
an exterior pocket attached to said exterior side of said abdominal binder;
a support strap having a proximate end, a distal end, an upper section, and middle section and a lower section, wherein said support strap is attached at said proximate end to said abdominal binder and wherein said upper section, said middle section and said lower section extend to said distal end of said support strap and respectively overlap said upper portion, said middle portion and said lower portion of said abdominal binder;
a support fastener selectively connecting said distal end of said support strap to said abdominal binder;
a first cross strap attached to said abdominal binder at said center region of said front section and having a first distal end extending toward said first side section, said first distal end further comprising a first fastener for selective connection to said exterior side of said abdominal binder; and
a second cross strap attached to said abdominal binder at said center region of said front section and having a second distal end extending toward said second side section, said second distal end further comprising a second fastener for selective connection to said exterior side of said abdominal binder.

40. The personal support device as in claim 39, wherein said abdominal binder is selected from a group of apparel consisting of a girdle and a pair of shorts.

41. The personal support device as in claim 39, wherein said interior pocket is attached to said center region of said front section, said interior pocket being closed at said lower portion of said abdominal binder and open toward said middle portion of said abdominal binder.

42. The personal support device as in claim 39, wherein said interior pocket is attached to said center region of said front section, said being closed at said middle portion of said abdominal binder and open toward said upper portion of said abdominal binder.

43. The personal support device as in claim 39, wherein said exterior pocket is closed toward said lower portion of said abdominal binder and open toward said upper portion of said abdominal binder.

44. The personal support device as in claim 39, wherein proximate end of said support strap is attached toward said first side of said abdominal binder and said distal end of said support strap overlaps said center region of said front section and extends toward said second side of said abdominal binder for said selective connection to said abdominal binder.

45. The personal support device as in claim 39, wherein said first cross strap further comprises a first lower cross strap and a first middle cross strap respectively attached at said lower portion and said middle portion of said center region, wherein said second cross strap further comprises a second lower cross strap and a second middle cross strap respectively attached at said lower portion and said middle portion of said center region, and wherein said first fastener and said second fastener respectively connect said first distal end and said second distal end above said lower portion of said center section.

46. The personal support device as in claim 39, wherein said first cross strap further comprises a first lower cross strap and a first middle cross strap respectively attached at said middle portion and said upper portion of said center region, wherein said second cross strap further comprises a second lower cross strap and a second middle cross strap respectively attached at said middle portion and said upper portion of said center region, and wherein said first fastener and said second fastener respectively connect said first distal end and said second distal end above said middle portion of said center section.

47. The personal support device as in claim 39, wherein at least one of said abdominal binder, said first cross strap, said second cross strap, said support strap, said interior pocket and said exterior pocket are further comprised of an elastic material.

48. The personal support device as in claim 39, wherein said abdominal binder, said first cross strap, said second cross strap, said support strap, said interior pocket and said exterior pocket are each comprised of an elastic material.

49. The personal support device as in claim 39, further comprising an inelastic padding material attached to said abdominal binder in said center region, said distal end of said support strap overlapping at least a portion of said inelastic padding material.

50. A binder for a human body comprising:
an abdominal binder selected from a group of apparel consisting of a girdle and a pair of shorts, said abdominal binder comprising a front section located between a pair of side sections and opposite a back section, said front section comprising a center region with an upper portion, a middle portion and a lower portion;
a first cross strap attached to said abdominal binder at said center region of said front section and comprising a first distal end extending towards and selectively fastened to one of said side sections at a first location above said lower portion, said first cross strap being attached to said center region below said upper portion;
a second cross strap attached to said abdominal binder at said center region of said front section and comprising a second distal end extending towards and selectively fastened to another of said side sections at a second location above said lower portion, said second cross strap being attached to said center region below said upper portion; and
a support strap attached to said abdominal binder, extending between said pair of side sections across said front section and selectively fastened at one of said side sections, wherein said support strap overlaps said upper portion, said middle portion and said lower portion of said abdominal binder and said first cross strap and said second cross strap are connected to said support strap.

51. The binder as in claim 50, wherein said upper portion, said middle portion and lower portion of said center region are relatively equal in width, wherein said first cross strap is approximately as wide as at least one of said lower portion and said middle portion, and wherein said second cross strap approximately as wide as at least one of said lower portion and said middle portion.

* * * * *